(12) United States Patent
Thornberry

(10) Patent No.: US 8,494,825 B2
(45) Date of Patent: Jul. 23, 2013

(54) COMPUTER-GUIDED SYSTEM FOR ORIENTING THE ACETABULAR CUP IN THE PELVIS DURING TOTAL HIP REPLACEMENT SURGERY

(76) Inventor: Robert L. Thornberry, Tallahassee, FL (US)

( * ) Notice: Subject to any disclaimer, the term of this patent is extended or adjusted under 35 U.S.C. 154(b) by 380 days.

(21) Appl. No.: 12/404,218

(22) Filed: Mar. 13, 2009

(65) Prior Publication Data

US 2009/0289806 A1 Nov. 26, 2009

Related U.S. Application Data

(60) Provisional application No. 61/069,267, filed on Mar. 13, 2008, provisional application No. 61/134,994, filed on Jul. 16, 2008.

(51) Int. Cl.
*G06G 7/48* (2006.01)
*A61B 17/42* (2006.01)

(52) U.S. Cl.
USPC .............................................. 703/7; 606/130

(58) Field of Classification Search
USPC .............................................. 703/7; 606/130
See application file for complete search history.

(56) References Cited

U.S. PATENT DOCUMENTS

| | | | |
|---|---|---|---|
| 6,033,415 A * | 3/2000 | Mittelstadt et al. | 606/130 |
| 6,205,411 B1 * | 3/2001 | DiGioia et al. | 703/11 |
| 6,322,565 B1 | 11/2001 | Garner et al. | |
| 6,723,102 B2 | 4/2004 | Johnson et al. | |
| 7,313,430 B2 | 12/2007 | Urquhart et al. | |
| 2004/0153079 A1 * | 8/2004 | Tsougarakis et al. | 606/77 |
| 2004/0230199 A1 | 11/2004 | Jansen et al. | |
| 2004/0243148 A1 | 12/2004 | Wasielewski | |
| 2005/0085822 A1 | 4/2005 | Thornberry et al. | |
| 2005/0119639 A1 | 6/2005 | McCombs et al. | |
| 2005/0240275 A1 | 10/2005 | Chappuis | |
| 2006/0142657 A1 * | 6/2006 | Quaid et al. | 600/424 |
| 2007/0260253 A1 | 11/2007 | Johnson et al. | |
| 2007/0276394 A1 | 11/2007 | Johnson et al. | |
| 2007/0287911 A1 | 12/2007 | Haid et al. | |
| 2008/0004633 A1 | 1/2008 | Arata et al. | |
| 2008/0039716 A1 | 2/2008 | Tuma | |

\* cited by examiner

*Primary Examiner* — Dwin M Craig
(74) *Attorney, Agent, or Firm* — Pandiscio & Pandiscio

(57) ABSTRACT

A method for determining the orientation of a first object in space, wherein the first object is interactive with a second object, the method comprising the steps of:

using kinematic action to generate a first data set reflective of the current spatial relationship between the first object and the second object; and comparing the first data set with a database of known data sets reflective of known spatial relationships between the first object and the second object in space so as to identify the current orientation of the first object in space.

13 Claims, 16 Drawing Sheets

COMPUTER-GUIDED SYSTEM FOR ORIENTING THE ACETABULAR CUP IN THE PELVIS DURING TOTAL HIP REPLACEMENT SURGERY

REFERENCE TO PENDING PRIOR PATENT APPLICATIONS

This patent application:

(i) claims benefit of prior U.S. Provisional Patent Application Ser. No. 61/069,267, filed Mar. 13, 2008 by Robert C. Thornberry for COMPUTER-GUIDED SYSTEM FOR ORIENTING THE ACETABULAR CUP IN THE ACETABULUM DURING TOTAL HIP REPLACEMENT SURGERY; and (ii) claims benefit of prior U.S. Provisional Patent Application Ser. No. 61/134,994, filed Jul. 16, 2008 by Robert C. Thornberry for COMBINED USE OF SIMULATION AND NAVIGATION TO DEMONSTRATE HIP KINEMATICS.

The two above-identified patent applications are hereby incorporated herein by reference.

FIELD OF THE INVENTION

This invention relates to computer-guided surgery in general, and more particularly to computer-guided surgery for orienting the acetabular cup in the pelvis during total hip replacement surgery.

BACKGROUND OF THE INVENTION

Joint replacement surgery seeks to replace portions of a joint with prosthetic components so as to provide long-lasting function and pain-free mobility.

One joint which is commonly replaced, in whole or in part, is the hip joint. The hip joint is located at the junction of the femur and the pelvis. More particularly, and looking now at FIG. 1, the head of the femur is received in the acetabulum of the pelvis, with a plurality of ligaments and other soft tissue serving to hold the bones in articulating relation.

During total hip replacement surgery, and looking now at FIG. 2, the operative elements of the hip joint (i.e., the head of the femur and the acetabulum) are replaced by prosthetic components. More particularly, during total hip replacement surgery, the head of the femur is replaced by a prosthetic ball-and-stem, and the natural acetabulum is replaced by a prosthetic acetabular cup, whereby to provide the prosthetic total hip joint.

In a partial hip replacement surgery, only one of the operative elements of the hip joint may be replaced, e.g., the head of the femur.

The present invention will hereinafter be discussed in the context of a total hip replacement surgery, however, it should also be appreciated that the present invention may be equally applicable to a partial hip replacement surgery (e.g., a unipolar hip replacement surgery, a bipolar hip replacement surgery, etc.) or a resurfacing procedure, etc.

In order to replace the head of the femur with the femoral prosthesis, the head of the femur is first distracted from the acetabulum so as to expose the femoral head. Then an osteotomy is performed on the femoral neck so as to remove the neck and head of the femur from the remainder of the femur. Next, the proximal end of the intramedullary canal is prepared so as to receive the stem of the femoral prosthesis. More particularly, a rasp, reamer, broach, etc. is used to hollow out, clean and enlarge the intramedullary canal of the femur so as to create a cavity to receive the stem of the femoral prosthesis. Then the stem of the femoral prosthesis is inserted into the intramedullary canal so that the ball of the femoral prosthesis is appropriately presented to the acetabular cup. Typically, the ball of the femoral prosthesis is formed separately from the stem of the femoral prosthesis, and it is united with the stem of the femoral prosthesis at the time of use. Furthermore, it should also be appreciated that during the surgery itself, it is common to temporarily position a trial stem or broach in the femur, attach a trial ball or equivalent element, and then temporarily reduce the joint so as to confirm the reconstruction before the actual prosthetic stem is secured in position within the femur.

In order to replace the native acetabulum with the prosthetic acetabular cup, the native acetabulum is first prepared to receive the prosthetic acetabular cup. This generally involves reaming an appropriate seat in the pelvis to receive the prosthetic acetabular cup. Then the prosthetic acetabular cup is installed in the pelvis, and the distraction released, so that the ball of the femoral prosthesis can be seated in the acetabular cup. In this respect it will be appreciated that the prosthetic acetabular cup typically comprises a metal cup and a liner made out of a polymer or a ceramic or a metal. The metal cup is configured so as to seat in the pelvis and oseointegrate into the host bone, and the liner is configured so as to provide a low-friction seat for the ball of the femoral prosthesis.

During seating of the acetabular cup in the pelvis, it is important that the acetabular cup be set in the pelvis with the proper positioning, i.e., at the proper location and with the proper orientation. Such proper positioning is important in order to (i) avoid impingement between the rim of the cup and the femoral prosthesis as the joint is moved through a range of motions, since such impingement can result in a reduced range of motion, excessive wear, joint failure and/or substantial pain for the patient, and (ii) avoid dislocation of the ball of the femoral prosthesis from the acetabular cup as the joint is moved through a range of motions, since such dislocation can result in damage to the anatomy, joint failure and/or substantial pain for the patient.

In many cases, the surgeon seats the prosthetic acetabular cup in the pelvis "by eye", and thereafter confirms the proper disposition of the cup when the distracted joint is subsequently reduced. However, this approach relies heavily on the anatomical view available to, and appreciated by, the surgeon, and errors in cup orientation (i.e., tilt) may not be discovered until after the surgery has been completed, since such errors in cup orientation can be difficult to detect interoperatively, even with the use of X-rays.

For this reason, various computer-guided systems have been developed to assist the surgeon in the proper placement of the acetabular cup during total hip replacement surgery. However, such computer-guided systems frequently require that a CT scan be made of the patient in advance of the procedure so as to determine the geometry of the acetabulum/pelvis. Furthermore, such computer-guided systems typically require the registration of pelvic anatomical landmarks (e.g., the pubic tubercles and the anterior/superior iliac spines), and the registration of femoral anatomical landmarks, with trackers (e.g., optical, electric/magnetic field, etc.). However, in practice, one or more of these pelvic anatomical landmarks can be difficult to acquire. Furthermore, the trackers must typically be applied to both the pelvis and the femur during the surgery itself so as to track the dispositions of these body parts during the surgery. These requirements can add to the cost of the procedure, can lengthen the time required for the procedure, and can be inconvenient for the surgeon (e.g., such as where the surgeon must work around optical trackers protruding into the surgical field).

Accordingly, there is a need for a new and improved computer-guided system for orienting the acetabular cup in the pelvis during total hip replacement surgery, wherein the requirement for a pre-operative CT scan is eliminated, and wherein the requirement for the acquisition of pelvic landmarks is eliminated.

In addition, there is also a need for a new and improved computer-guided system which can be used to orient prosthetic components other than the acetabular cup, e.g., a computer-guided system which can be used to orient a femoral component.

Furthermore, there is also a need for a new and improved computer-guided system which can be used to orient prosthetic components for joints other than the hip, e.g., a computer-guided system which can be used to orient prosthetic components in the knee.

And there is a need for a new and improved computer-guided system which can be used to determine and adjust the position of substantially any two interacting components in space.

SUMMARY OF THE INVENTION

These and other objects are addressed by the provision and use of the present invention, which comprises a new and improved computer-guided system for orienting the acetabular cup in the pelvis during total hip replacement surgery, wherein the requirement for a pre-operative CT scan is eliminated (but may still be provided if desired), and wherein the requirement for the acquisition of pelvic landmarks is eliminated (but may still be provided if desired).

More particularly, with the present invention, the surgeon first sets the prosthetic acetabular cup into the pelvis in the conventional manner (e.g., "by eye"). The surgeon then uses the new computer-guided system of the present invention to: (i) detect the current spatial relationship between the acetabular cup and the femur using kinematic action; (ii) compare the current spatial relationship between the acetabular cup and the femur to the desired (i.e., "ideal") spatial relationship between the acetabular cup and the femur (e.g., so as to minimize the aforementioned impingement and dislocation problems); and (iii) adjust the current orientation of the acetabular cup with a device so as to set the acetabular cup with the desired orientation.

Significantly, this is achieved without requiring a pre-operative CT scan (although one may still be provided if desired), and without requiring the acquisition of pelvic landmarks (although they may still be provided if desired).

In addition, the present invention also provides a new and improved computer-guided system which can be used to orient prosthetic components other than the acetabular cup, e.g., a computer-guided system which can be used to orient a femoral component.

Furthermore, the present invention also provides a new and improved computer-guided system which can be used to orient prosthetic components for joints other than the hip, e.g., a computer-guided system which can be used to orient prosthetic components in the knee.

And the present invention also provides a new and improved computer-guided system which can be used to determine and adjust the position of substantially any two interacting components in space.

In one preferred form of the invention, there is provided a method for determining the orientation of a first object in space, wherein the first object is interactive with a second object, the method comprising the steps of:

using kinematic action to generate a first data set reflective of the current spatial relationship between the first object and the second object; and comparing the first data set with a database of known data sets reflective of known spatial relationships between the first object and the second object in space so as to identify the current orientation of the first object in space.

In another form of the present invention there is provided a system for determining the orientation of a first object in space wherein the first object is interactive with a second object, the system comprising:

apparatus configured to use kinematic action to generate a first data set reflective of the current spatial relationship between the first object and the second object; and apparatus for comparing the first data set with a database of known data sets reflective of known spatial relationships between the first object and the second object in space so as to identify the current orientation of the first object in space.

In another form of the present invention there is provided an acetabular cup comprising:

a hollow cup having an outer surface for attachment to the pelvis and an inner surface for receiving a ball of a femur;

the outer surface comprising longitudinal ridges for permitting selective movement of the cup relative to the pelvis.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein.

DETAILED DESCRIPTION OF THE PREFERRED EMBODIMENTS

Figure 1:
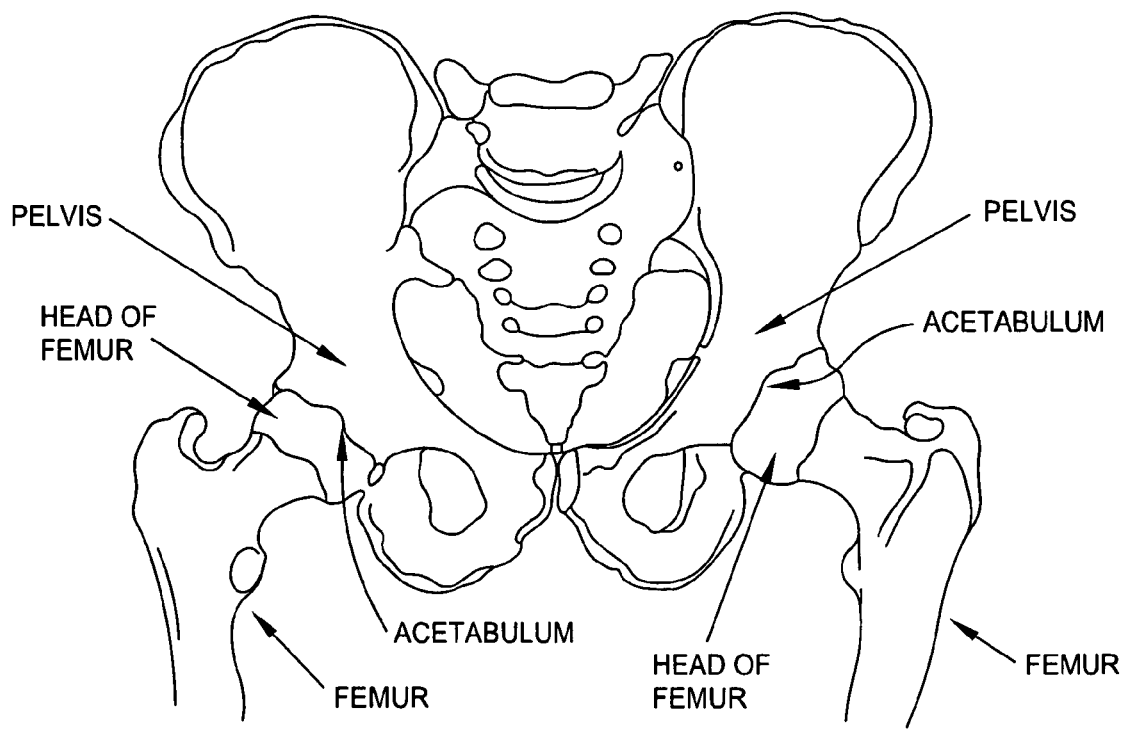
FIG. 1 is a schematic view of the hip joints.
Figure 2:
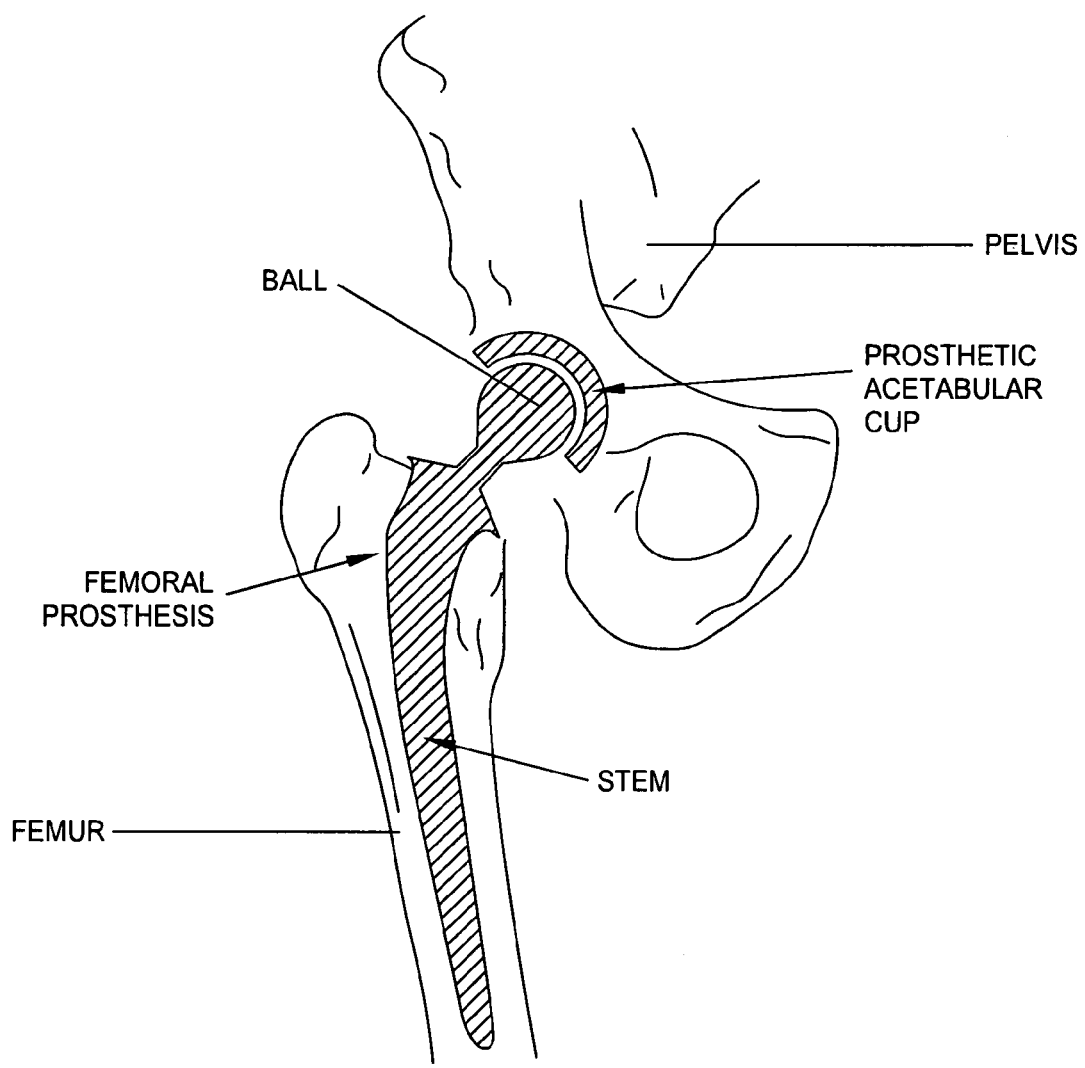
FIG. 2 is a schematic view showing a total hip replacement.
Figure 3:
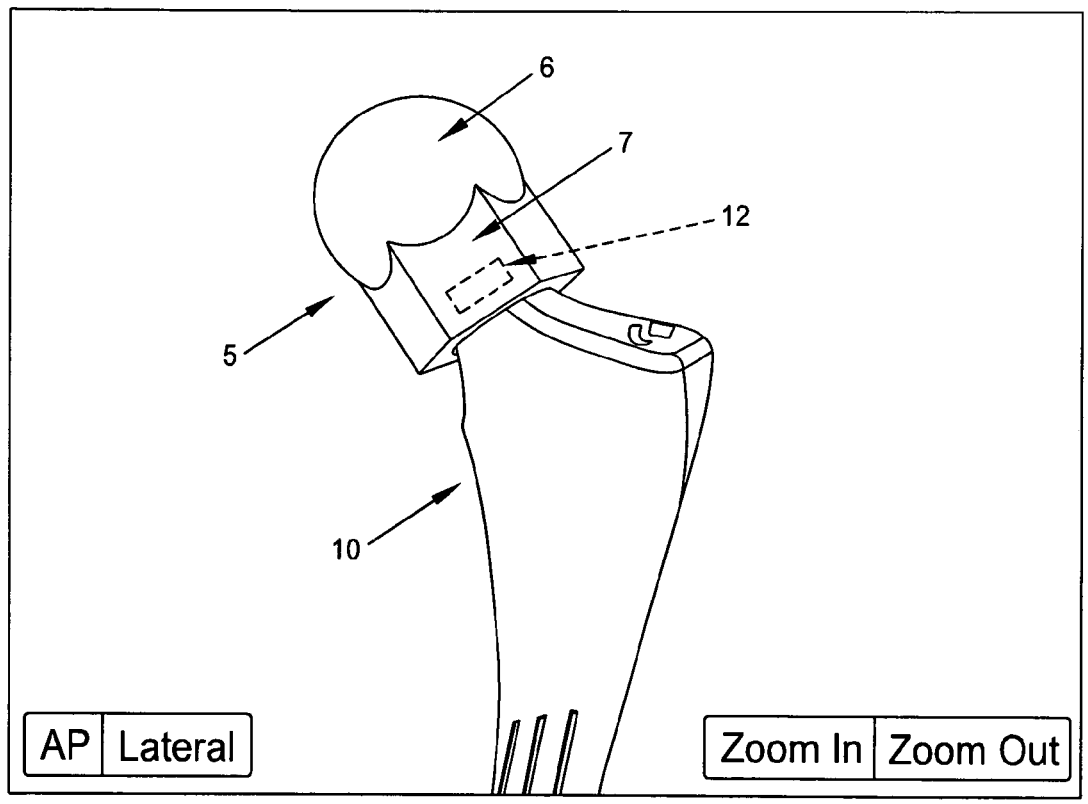
FIGS. 3 and 4 are schematic views showing an impinger mounted to a broach or femoral stem.
Figure 4:
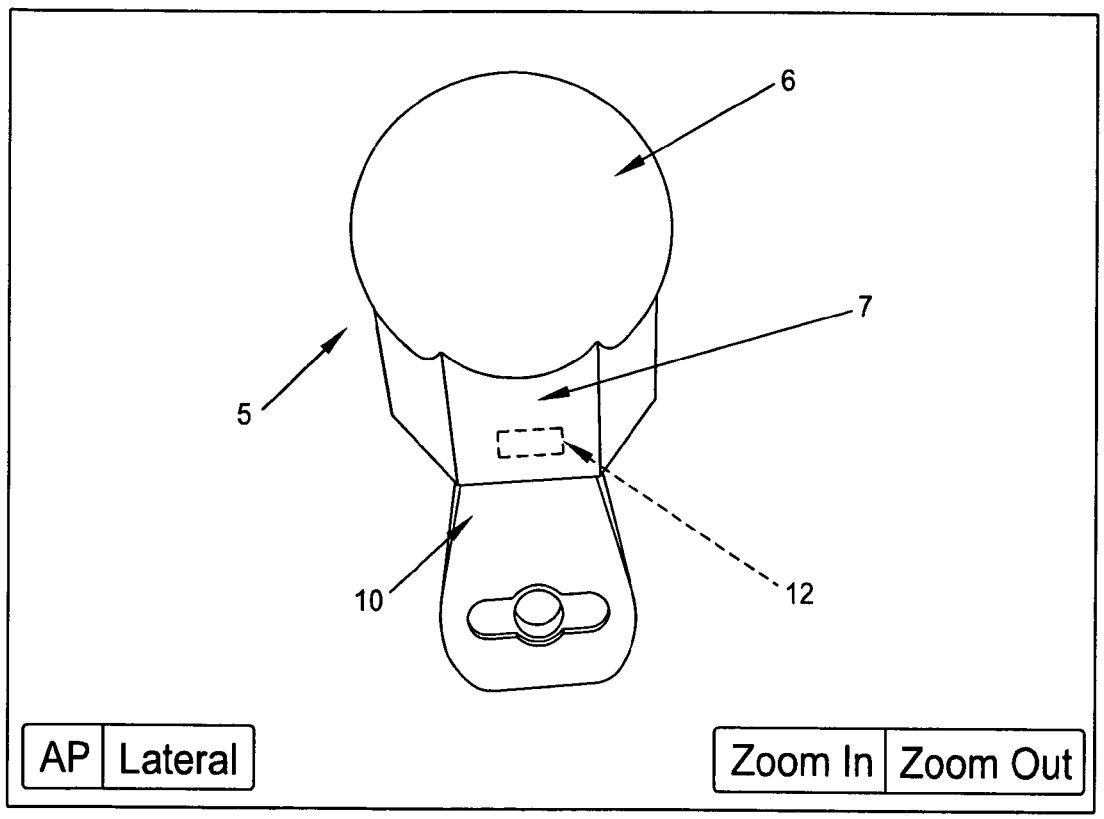
Figure 5:
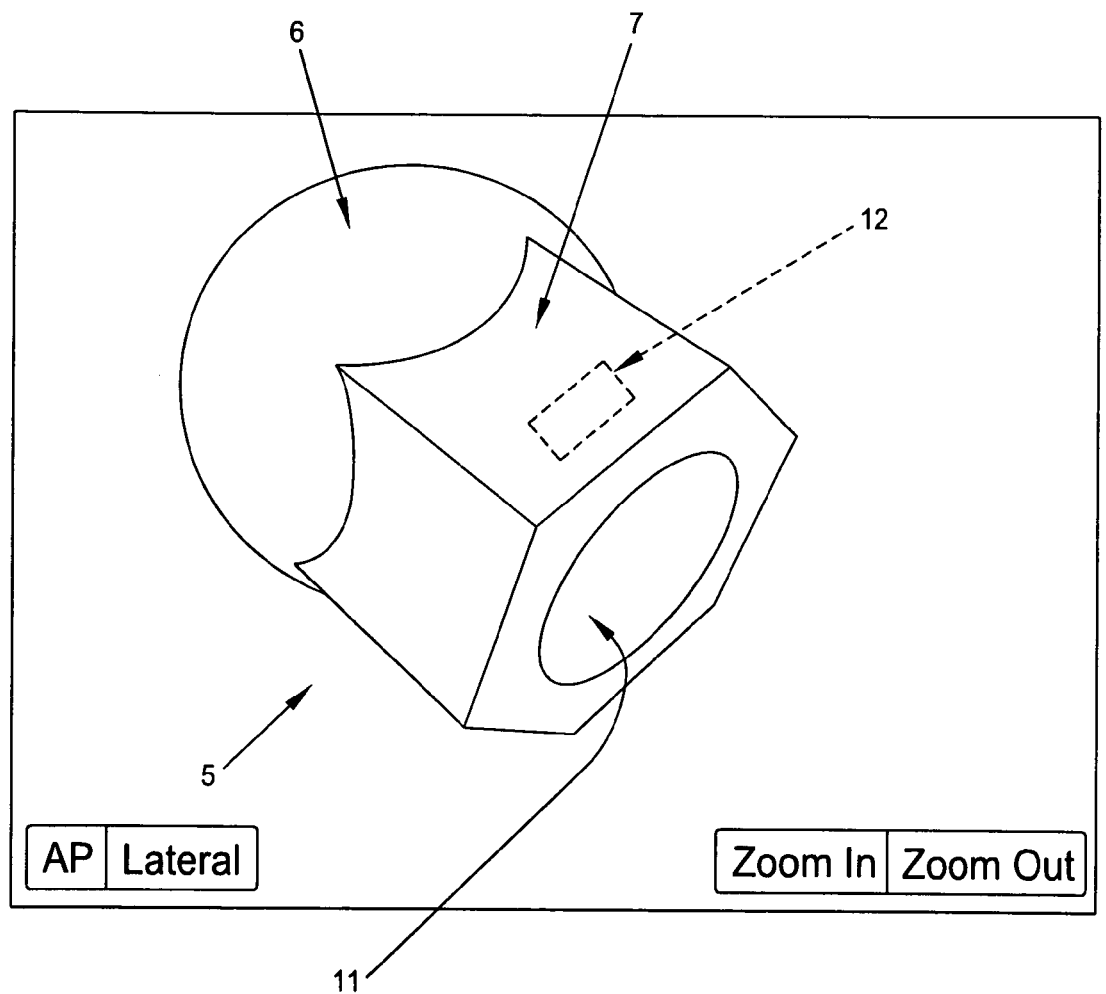
FIGS. 5-7 are schematic views showing further details of the impinger shown in FIGS. 3 and 4.
Figure 6:
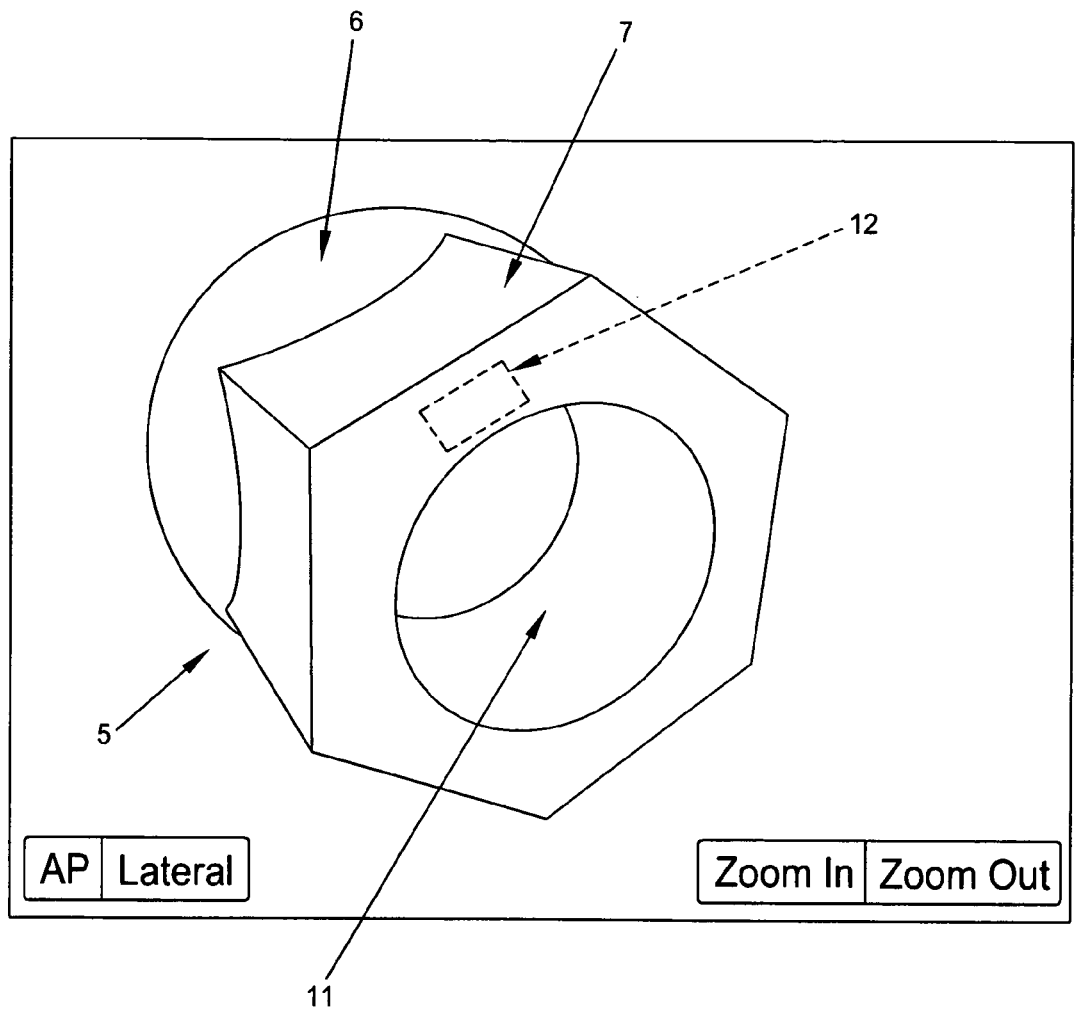
Figure 7:
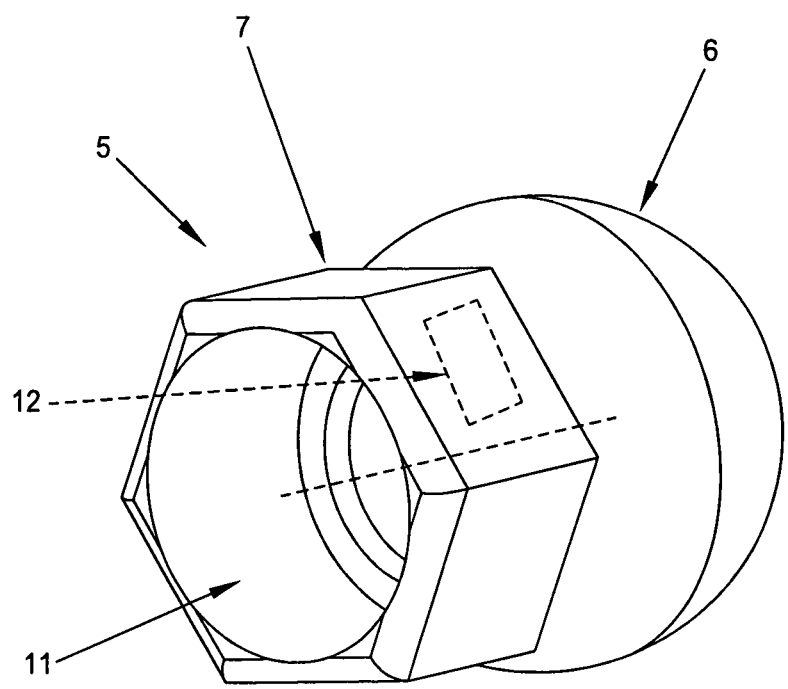

The present invention comprises a new and improved computer-guided system for orienting the acetabular cup in the pelvis during total hip replacement surgery, wherein the requirement for a pre-operative CT scan is eliminated (but may still be provided if desired), and wherein the requirement for the acquisition of pelvic landmarks is eliminated (but may still be provided if desired).

More particularly, with the present invention, the surgeon first sets the prosthetic acetabular cup into the pelvis in the conventional manner (e.g., "by eye"). The surgeon then uses the new computer-guided system of the present invention to: (i) detect the current spatial relationship between the acetabular cup and the femur using kinematic action; (ii) compare the current spatial relationship between the acetabular cup and the femur to the desired (i.e., "ideal") spatial relationship between the acetabular cup and the femur (e.g., so as to minimize the aforementioned impingement and dislocation problems); and (iii) adjust the current orientation of the acetabular cup with a device so as to set the acetabular cup with the desired orientation.

Significantly, this is achieved without requiring a pre-operative CT scan (although one may still be provided if desired), and without requiring the acquisition of pelvic landmarks (although they may still be acquired if desired).

In addition, the present invention also provides a new and improved computer-guided system which can be used to orient prosthetic components other than the acetabular cup, e.g., a computer-guided system which can be used to orient a femoral component.

Furthermore, the present invention also provides a new and improved computer-guided system which can be used to orient prosthetic components for joints other than the hip, e.g., a computer-guided system which can be used to orient prosthetic components in the knee.

And the present invention also provides a new and improved computer-guided system which can be used to determine and adjust the position of substantially any two interacting components in space.

(i) Detecting the Current Spatial Relationship Between the Acetabular Cup and the Femur Using Kinematic Action The present invention detects the current spatial relationship between the acetabular cup and the femur after the cup has been set in the pelvis by the surgeon. This is done by kinematic action.

More particularly, and looking now at FIGS. 3-7, an impinger 5, comprising a ball 6 and a neck 7, is mounted on a broach 10 which is used to prepare the intramedullary canal of the femur. To this end, neck 7 can include a recess 11 for receiving the broach. Alternatively, impinger 5 can be placed on the prosthetic stem, including both the temporary trial stem and the actual prosthetic stem. Impinger 5 includes a sensor 12 which allows the motion of the impinger to be determined in a standard 3D coordinate system.

Sensor 12 on impinger 5 may comprise one or more standard optical or electric/magnetic field sensors of the sort which can indicate absolute position (and hence the change in absolute position, i.e., motion) in a standard 3D coordinate system.

Alternatively, and more preferably, sensor 12 on impinger 5 may comprise one or more accelerometers, inclinometers, gyroscopes, magnetic compasses, cameras, etc., or a combination of the foregoing, which can indicate motion in a standard 3D coordinate system.

In either case, sensor 12 on impinger 5 is used to track the motion of impinger 5 within the standard 3D coordinate system.

Figure 8:
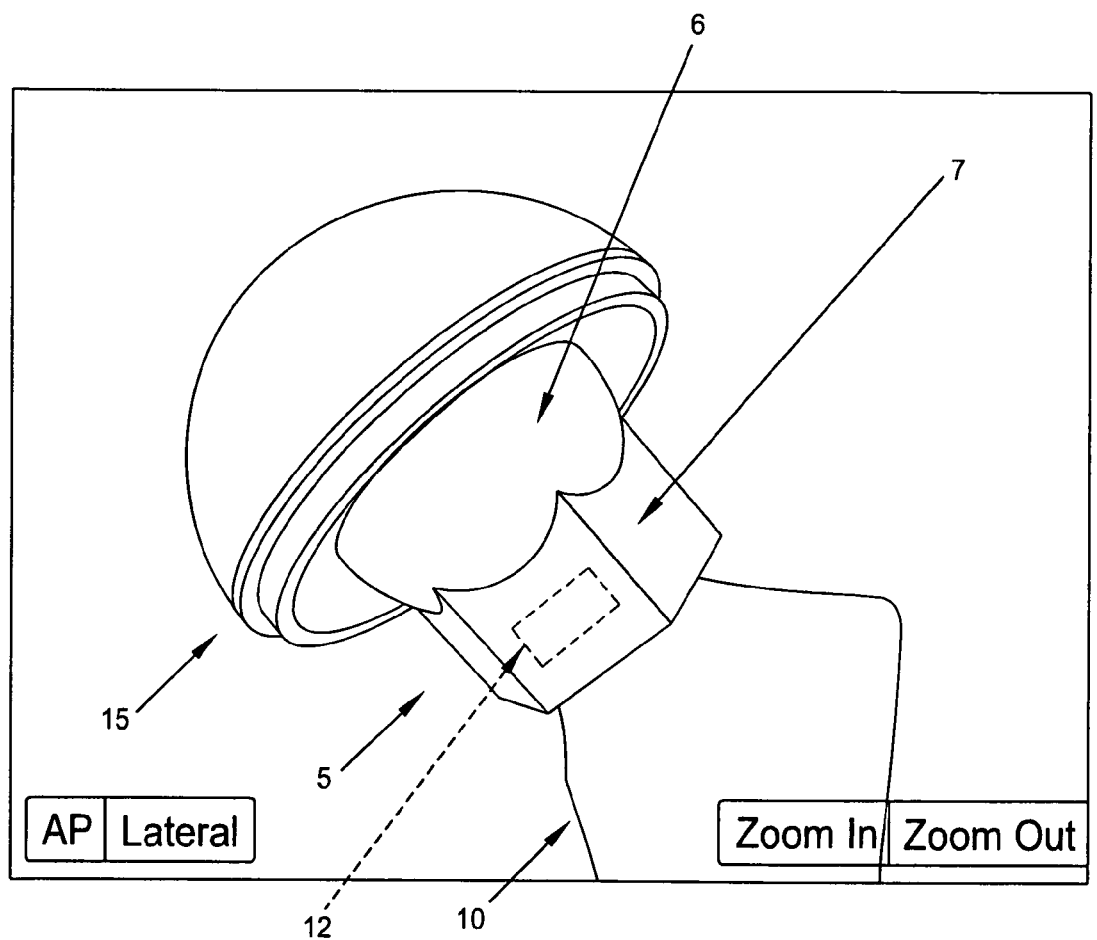
FIG. 8 is a schematic view showing the impinger of FIGS. 3 and 4 seated in an acetabular cup.

In accordance with the present invention, and looking now at FIG. 8, impinger 5 is used to dynamically engage the rim of the acetabular cup, in a kinematic manner, as the sensor tracks the motion of the impinger, whereby to generate a data set (e.g., a "data cloud") representative of the range of motion permitted between the impinger and the acetabular cup. This data cloud has a different, and unique, geometric configuration, depending on the actual spatial relationship existing between the acetabular cup and the impinger (which is attached to the femur). In other words, a data cloud having a first configuration will be generated when the acetabular cup has a first orientation relative to the dynamically moving impinger, another data cloud having a second configuration will be generated when the acetabular cup has a second orientation relative to the dynamically moving impinger, still another data cloud having a third configuration will be generated when the acetabular cup has a third orientation relative to the dynamically moving impinger, etc.

More particularly, after impinger 5 has been set on broach 10 and ball 6 of impinger 5 seated in acetabular cup 15, impinger 5 is moved about so that its neck 7 repeatedly engages, or "impinges", the rim of the acetabular cup so as to explore the range of motion permitted between impinger 5 and the acetabular cup. As this occurs, sensor 12 records the motion of impinger 5 so as to generate a data set, or data cloud, representative of the range of motion permitted between impinger 5 and acetabular cup 15. This data cloud has a unique configuration depending on the orientation of the acetabular cup relative to the dynamically moving impinger.

Figure 9:
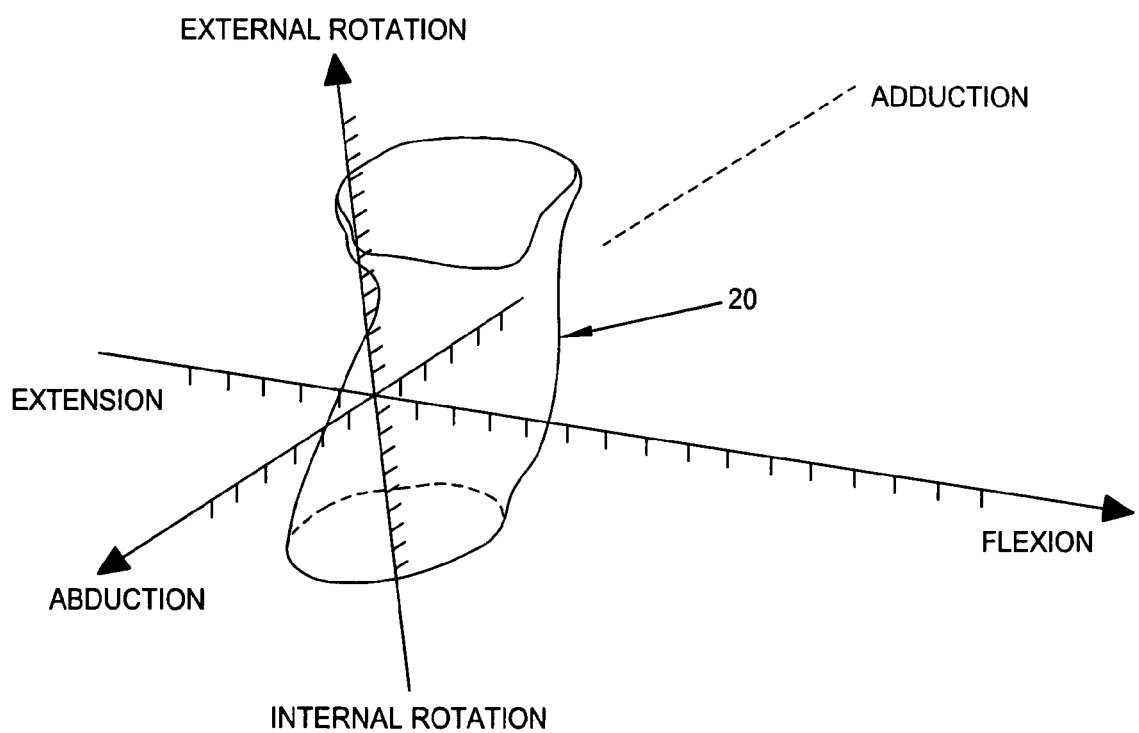
FIG. 9 is a schematic view showing an exemplary data cloud which is representative of the range of motion permitted between the impinger and the acetabular cup when those components are in a particular spatial relationship to one another.
Figure 9A:
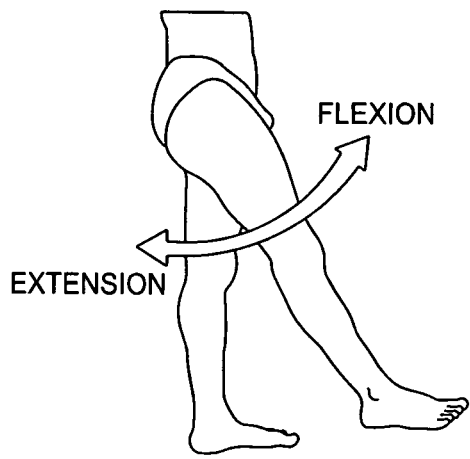
FIGS. 9A-9D are schematic views illustrating various types of leg motion.
Figure 9B:
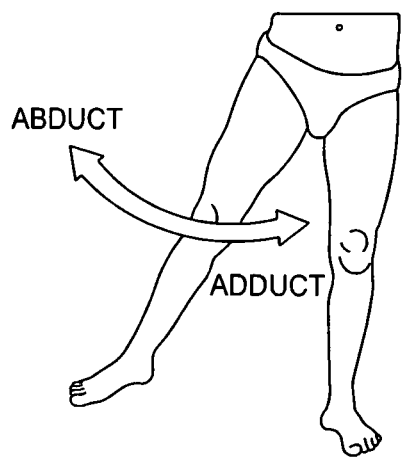
Figure 9C:
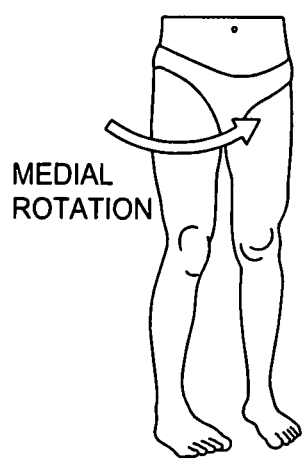
Figure 9D:
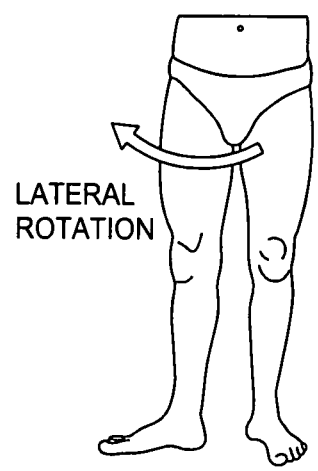

By forming neck 11 of impinger 5 with a complex geometric configuration (e.g., hexagonal, as shown in FIGS. 3-8, or any other configuration suitable for the purposes of the present invention), a unique data cloud can be created which is representative of the unique range of motion permitted between impinger 5 and acetabular cup 15 for a given cup disposition. See FIG. 9, which shows an exemplary data cloud 20 which is representative of the range of motion permitted between the impinger 5 and acetabular cup 15 when those components are in a particular relationship to one another. Note how the axes upon which data cloud 20 is plotted (see FIG. 9) relate to actual anatomical leg motion (see FIGS. 9A-9D).

More particularly, the femur (with tracked impinger 5 attached) is moved so as to establish an initial impingement point between impinger 5 and prosthetic acetabular cup 15. The position of impinger at this first impingement point is identified by sensor 12 (e.g., the optical tracker, electric/magnetic field tracker, accelerometers, inclinometers, etc.) and recorded. Then the femur is moved dynamically through a range of motions so as to allow impinger 5 to engage acetabular cup 15 at a plurality of other impingement points along the rim of the acetabular cup. As each impingement occurs, the location of impinger 5 is recorded by the sensor. This process is repeated until a sufficient number of impingement points have been identified, and the corresponding position of impinger 5 recorded, so that a data cloud can be generated which is representative of the range of motion permitted between the impinger and the acetabular cup, when those components are in a particular relationship to one another.

In essence, as each impingement point is identified and the corresponding location of the impinger recorded, a "data point" is created. These data points together form a data cloud containing all of the identified impingement points, which essentially identifies the range of motion permitted between the impinger and the acetabular cup, for the given spatial relationship existing between those components.

(ii) Comparing the Current Spatial Relationship Between the Acetabular Cup and the Femur to the Desired (i.e., "Ideal") Spatial Relationship Between the Acetabular Cup and the Femur Next, the current spatial relationship between the acetabular cup and the femur is compared with the desired (i.e., "ideal") spatial relationship between the cup and the femur, to determine if, and how, the acetabular cup should be moved (i.e., re-oriented) so as to achieve the desired (i.e., "ideal") orientation for the acetabular cup.

Figure 10:
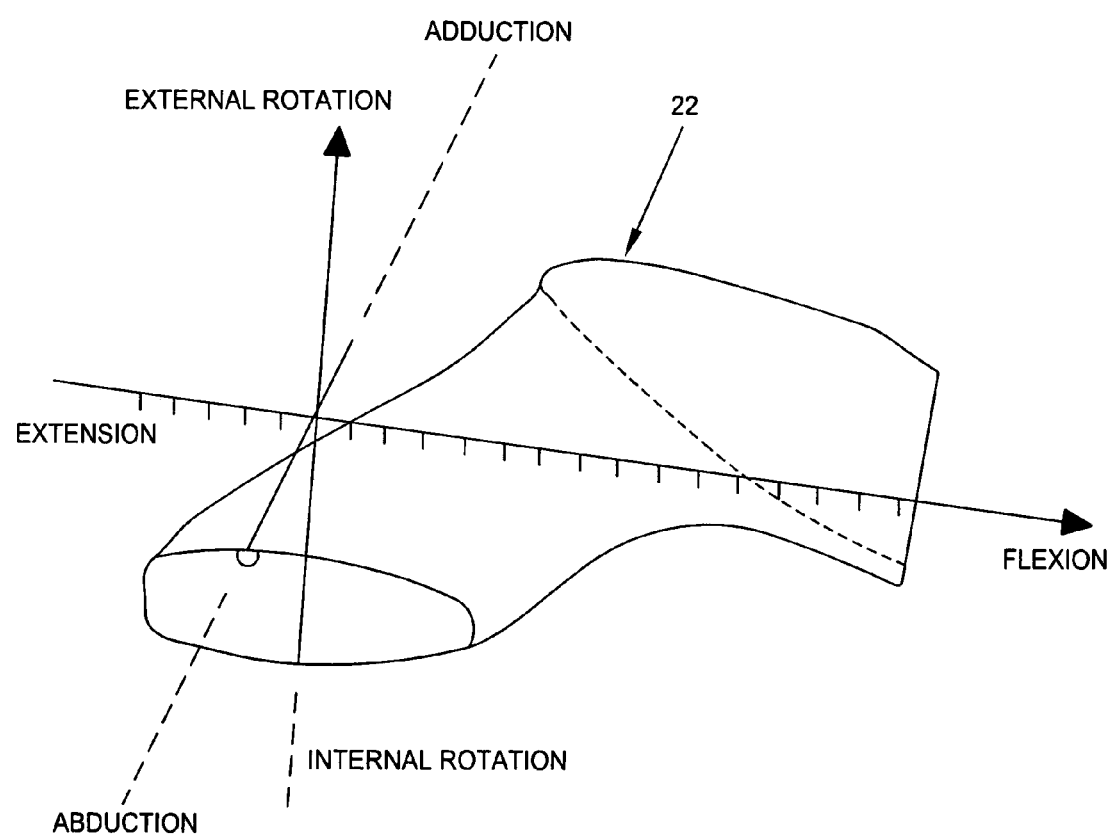
FIG. 10 is a schematic view showing an exemplary data cloud generated by a computer simulation performed in a virtual environment, or experimentally-derived in a laboratory environment, of the range of motion permitted between the impinger and the acetabular cup for a given acetabular cup orientation.

More particularly, as noted above, the data cloud generated by moving impinger 5 so that it impinges upon acetabular cup 15 at a plurality of locations yields a data cloud which has a unique geometry reflecting the range of movement permitted by the current spatial relationship between the acetabular cup and the impinger (which is attached to the femur). As a result, this data cloud can be compared against a database of data clouds of known ranges of motion for given acetabular cup orientations in an idealized joint so as to identify the current orientation of the acetabular cup in the operative field. This database of data clouds of known acetabular cup orientations may be generated by computer simulations that are performed in a virtual environment, or by experimentally deriving the data in a laboratory environment (e.g., in a cadaver lab), etc. See, for example, FIG. 10, which shows a data cloud 22 generated by a computer simulation performed in a virtual environment and which reflects the range of motion for a given spatial relationship between the acetabular cup and the femur. In other words, the patient-specific data cloud created through the aforementioned kinematic motion of impinger 5 impinging on acetabular cup 15 can be compared with a database of data clouds for known ranges of motion for given cup-femur relationships in an idealized joint so as to identify the current orientation of the acetabular cup in the operative field.

Various methods can be used to compare the patient-specific data cloud against the pre-recorded data clouds in the database so as to determine the relative orientation of the acetabular cup vis-à-vis the femur. These methods include, but are not limited to, mathematical and statistical methods, shape fitting/recognition methods, etc.

As a result of the foregoing, the current orientation of the acetabular cup can be determined, and hence any necessary adjustment to the current orientation of the acetabular cup can be determined.

Figure 11:
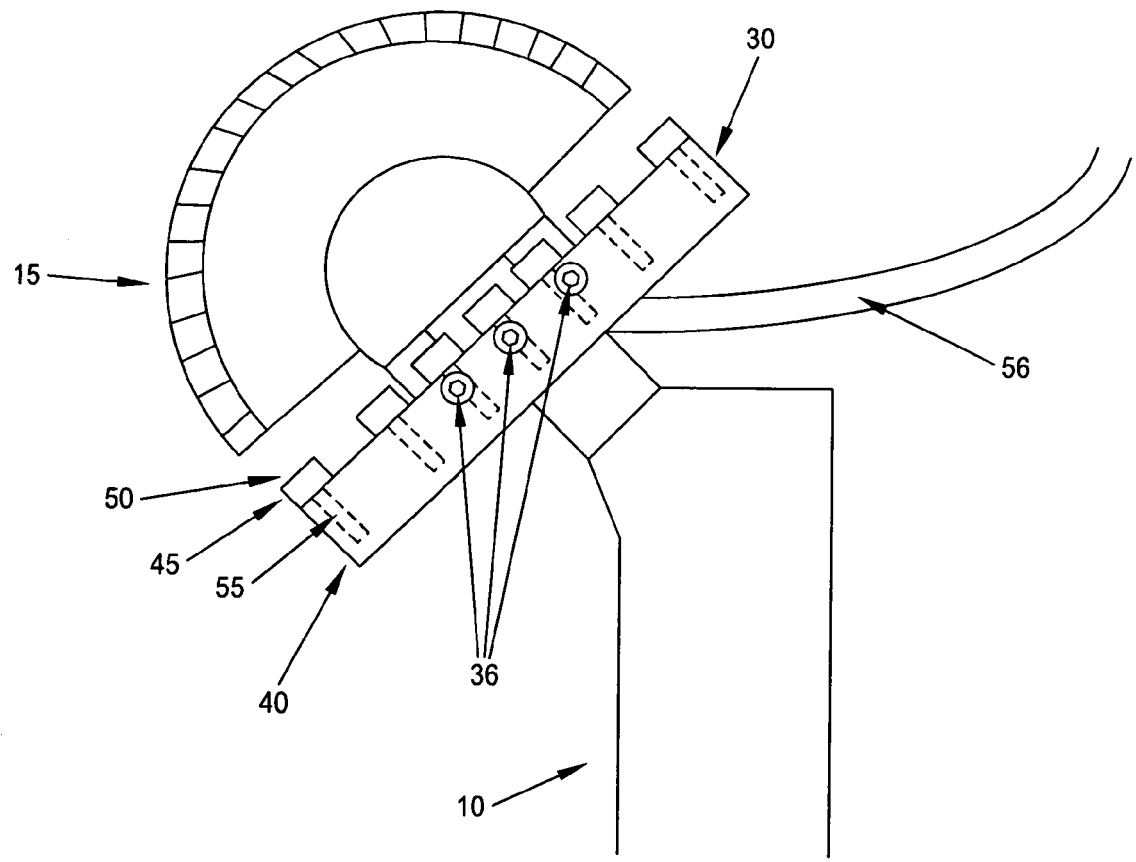
FIG. 11 is a schematic side view showing an impactor mounted to the impinger.
Figure 12:
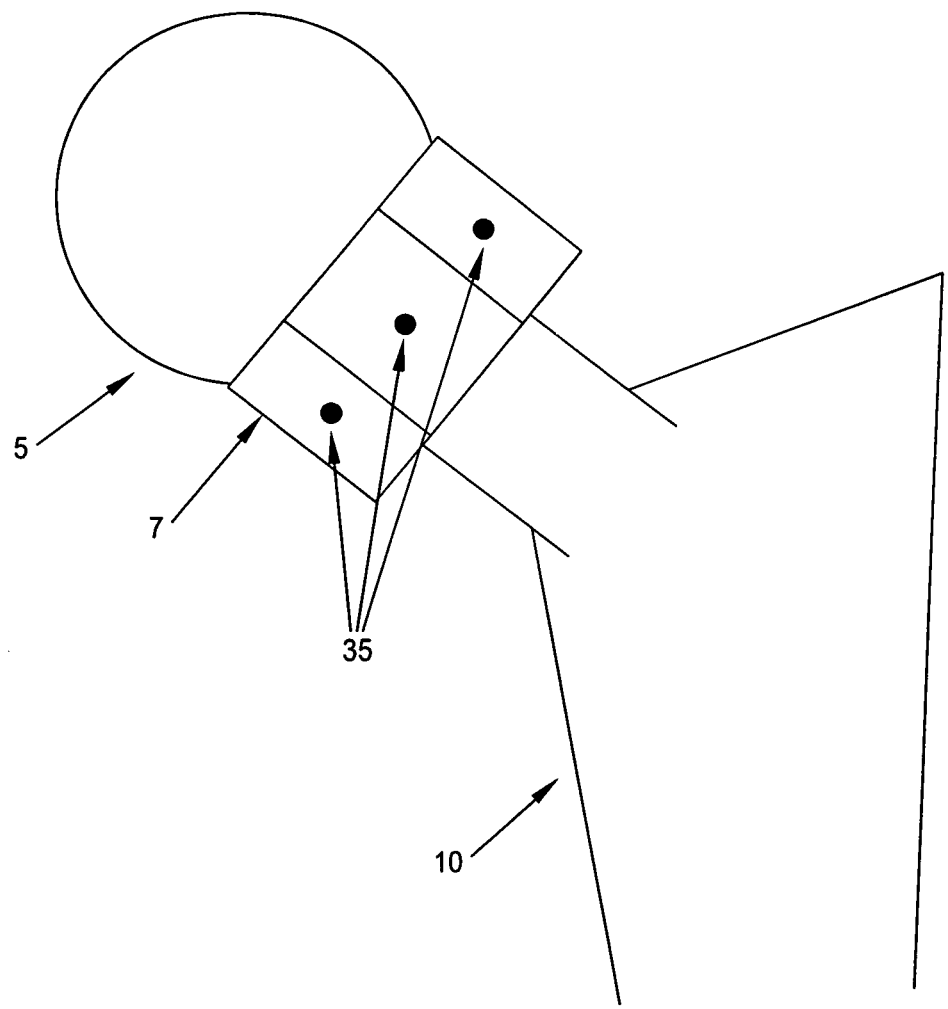
FIG. 12 is a schematic side view showing how the impinger mounts the impactor.
Figure 13:
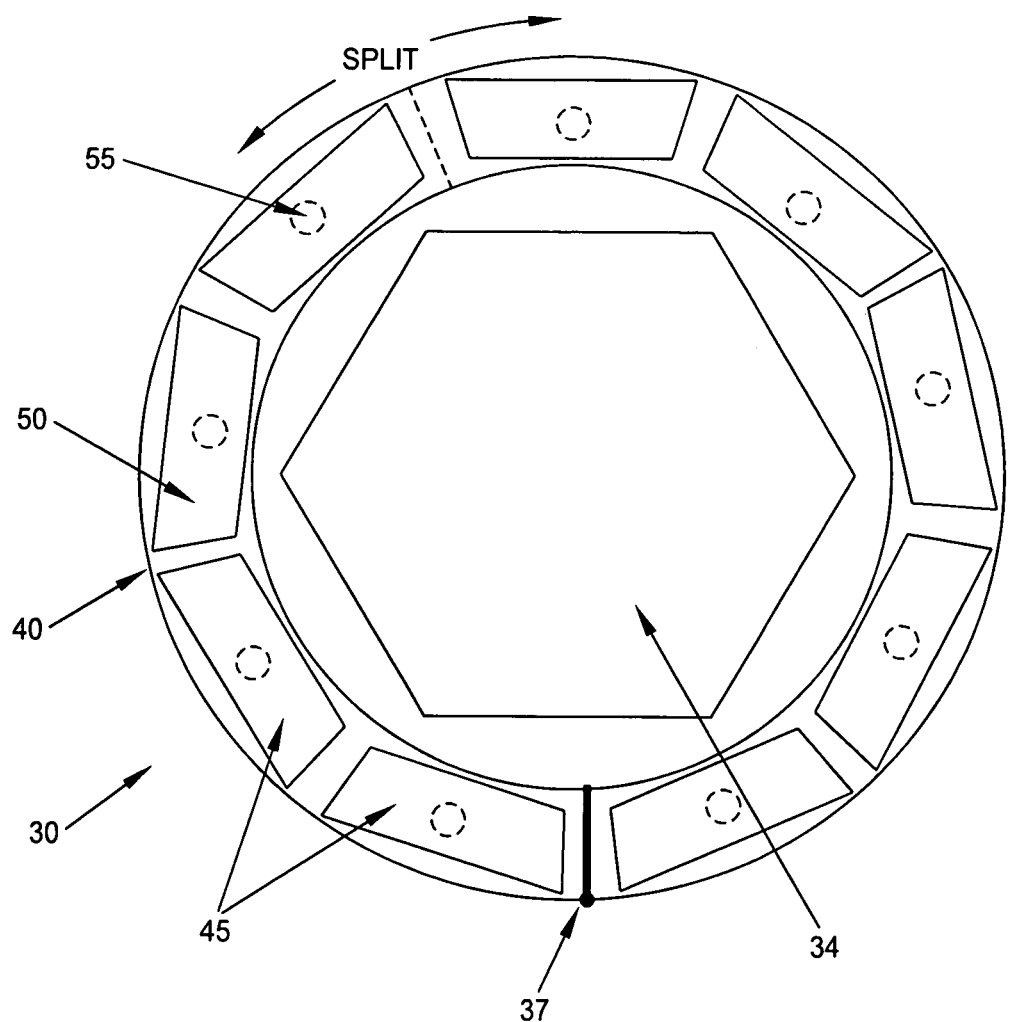
FIG. 13 is a schematic end view showing further details of the front face of the impactor.

(iii) Adjusting the Current Orientation of the Acetabular Cup with a Device so as to Set the Acetabular Cup with the Desired Orientation Once the current orientation of the acetabular cup has been compared to the desired (i.e., "ideal") orientation of the acetabular cup, so that it is known if, and how, the cup should be re-oriented in order to achieve the desired cup orientation, a device may be mounted to impinger 5 so as to urge the cup into the desired orientation. More particularly, and looking now at FIGS. 11-13, an impactor 30 is configured to be affixed to impinger 5 (which is itself still mounted to the broach or femoral stem 10) and to impact the rim of the acetabular cup so as to adjust the orientation of the acebabular cup within the pelvis. To this end, impactor 30 may be provided with a complementary geometry (i.e., a hexagonal recess 34) to fit over neck 7 of impinger 5, and impinger 5 may be provided with a plurality of holes 35 along its exterior surfaces (e.g., on neck 7) for receiving screws 36 of impactor 30. If desired, impactor 30 may be hinged as shown at 37 to allow the impactor to fit over neck 7 without having to dismount impinger 5 from broach 10.

The impactor itself comprises a body 40 which is generally circular in shape and comprises a plurality of impacting units 45 along its perimeter for engaging appropriate portions of the acetabular cup and urging the cup into the desired orientation. Impacting units 45 preferably comprise impacting pads 50 which are mounted on actuating rods 55. Actuating rods 55 move impacting pads 50 away from body 40 of the impactor so as to selectively engage specific portions of the rim of the acetabular cup and thereby urge the cup into the proper orientation. Actuating rods 55 may be actuated pneumatically, e.g., via a pneumatic hose 56.

Using the acquired information about the positions of the acetabular cup and the femur, the impactor is able to actuate the actuating rods and drive their respective impacting pads as appropriate so as to properly orient the acetabular cup vis-à-vis the femur, and hence vis-à-vis the pelvis.

Once the acetabular cup has been moved into the desired orientation, the impactor can be removed from the impinger, and then the impinger can be removed from the broach or femoral stem, whereupon the hip replacement surgery can be completed in the conventional manner.

Figure 14:
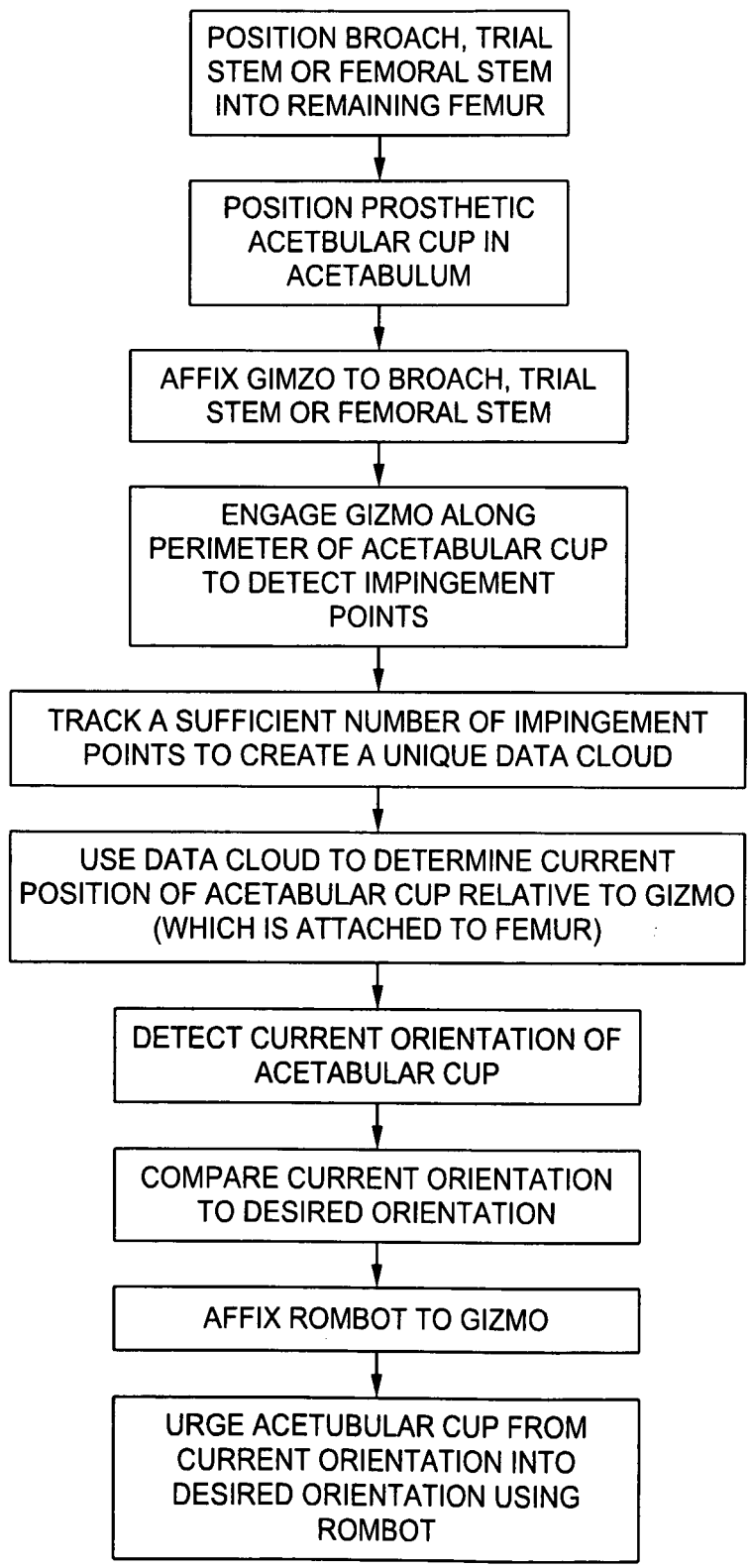
FIG. 14 is a flow chart illustrating one preferred method of the present invention.

FIG. 14 is a flowchart illustrating one preferred method for orienting the acetabular cup in the acetabulum during total hip replacement surgery.

Additional Constructions

Figure 15:
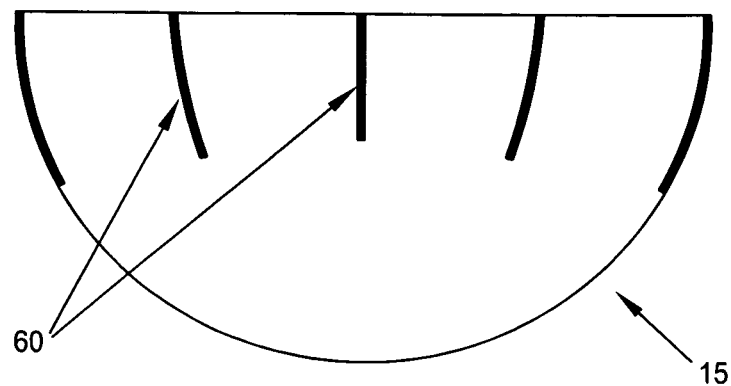
FIGS. 15 and 16 are schematic side views showing a novel form of acetabular cup.
Figure 16:
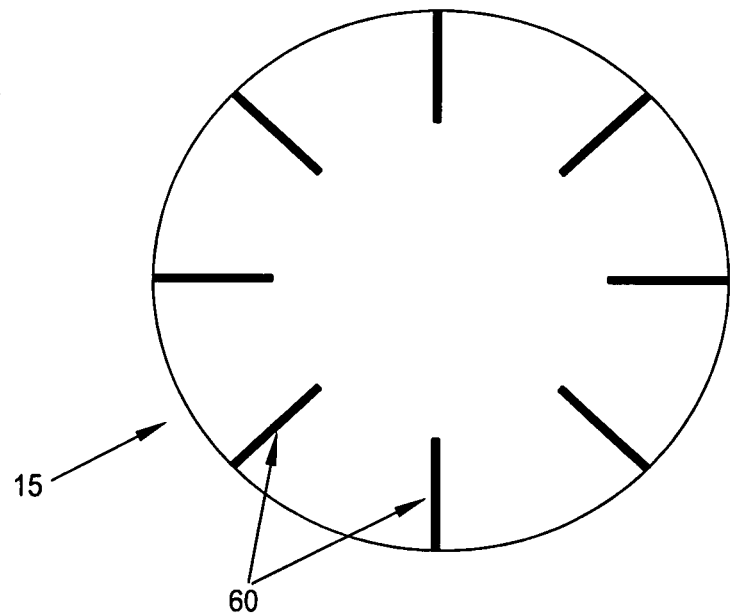

In another form of the present invention, a novel prosthetic acetabular cup is provided, wherein the novel prosthetic cup has a configuration which facilitates proper orienting of the cup using the impactor. More particularly, the novel acetabular cup comprises a geometry which allows rigid, but adjustable, orienting within the acetabulum. More particularly, and looking now at FIGS. 15 and 16, the acetabular cup may be provided with longitudinal ridges 60 which extend part way along the exterior of the cup. These ridges allow the impactor to adjust portions of the cup into the correct plane without allowing movement of the cup in other directions. Additionally, these ridges allow the impactor to more precisely push in, or lever out, the cup relative to the bony acetabulum when and where necessary.

Application of the Invention to Other Prosthetic Components of the Hip, to Other Joints, and to Other Interacting Objects in Space It should be appreciated that the present invention also provides a new and improved computer-guided system which can be used to orient prosthetic components other than the acetabular cup, e.g., the present invention can be used to orient a femoral component for the hip.

Furthermore, the present invention can also be used to orient prosthetic components for joints other than the hip, e.g., the present invention provides a computer-guided system which can be used to orient prosthetic components in the knee.

And the present invention can be used to determine and adjust the position of substantially any two interacting components in space.

Thus it will be seen that the present invention provides a new and unique method for accurately identifying the orientation of linked objects in space. This new method uses highly accurate computer simulations that are performed in a virtual environment, or uses experimentally-derived laboratory data, allowing complete data collection of all possible orientations of the linked objects in question when subjected to movement. These orientation data sets (e.g., data clouds) are then stored for later use as a reference for relating the data obtained in the "real world" when kinematically moving the linked objects relative to each other (or relative to a fixed standard). The "real world" data so obtained, when compared to the reference "simulation data" (or experimentally-derived data) can reliably "solve for" (i.e., indicate) the true orientation of the linked objects in space to one another, which in many cases could not otherwise be obtained. The aforementioned kinematic motions of the objects create the large data sets that increase the accuracy of this method over other, more conventional "static" methods.

Furthermore, it will be appreciated that once the true orientation of the linked objects in space has been determined, forces can be applied to one or more of the objects so as to re-orient them.

This new and robust functionality has usefulness in many applications, e.g., such as the aforementioned acetabular cup orientation obtained by using the impinger device. Furthermore, the method of the present invention can be used to place an acetabular cup in the pelvis with no impactor device. And the method of the present invention can be used to determine the proper orientation of implants in, for example, the knee joint, and allows intra-operative real-time modification that improves the restoration of more normal knee kinematics. Many other applications will be apparent to those skilled in the art in view of the present disclosure.

Modifications of the Preferred Embodiments

It should be understood that many additional changes in the details, operation, steps and arrangements of elements, which have been herein described and illustrated in order to explain the nature of the present invention, may be made by those skilled in the art while still remaining within the principles and scope of the invention.

What is claimed is:

1. A method for (i) determining the orientation of a first joint prosthesis vis-à-vis a second, mating joint prosthesis, and (ii) adjusting the orientation of the first joint prosthesis vis-à-vis the second, mating joint prosthesis when appropriate, the method comprising the steps of:

providing a database comprising a plurality of different pre-determined data sets, wherein each of the plurality of different pre-determined data sets correlates to a range of motion permitted between the first joint prosthesis and the second, mating joint prosthesis when the first joint prosthesis and the second, mating joint prosthesis have a particular spatial relationship vis-à-vis one another;

moving the second, mating joint prosthesis while in engagement with the first joint prosthesis so as to generate an actual data set which correlates to a range of motion permitted between the first joint prosthesis and the second, mating joint prosthesis given the actual spatial relationship between the first joint prosthesis and the second joint prosthesis;

comparing the actual data set with the plurality of different pre-determined data sets in the database so as to identify the actual orientation of the first joint prosthesis vis-à-vis the second, mating joint prosthesis; and adjusting the actual orientation of the first joint prosthesis vis-à-vis the second, mating joint prosthesis when appropriate using a device mounted to the second, mating joint prosthesis.

2. A method according to claim 1 wherein moving the second, mating joint prosthesis while in engagement with the first joint prosthesis comprises moving the second, mating joint prosthesis so that the second, mating joint prosthesis dynamically engages the first joint prosthesis at a plurality of impingement locations.

3. A method according to claim 2 wherein the second, mating joint prosthesis is configured so as to yield a different, and unique, actual data set for each possible spatial relationship which may exist between the first joint prosthesis and the second, mating joint prosthesis.

4. A method according to claim 2 wherein the database of different pre-determined data sets comprises data sets generated by at least one of the group consisting of: (i) computer simulations that are performed in a virtual environment, and (ii) experimentally-derived laboratory data.

5. A method according to claim 2 wherein the step of comparing the actual first data set with a database of different pre-determined data sets is conducted using at least one from the group consisting of: (i) mathematical methods, (ii) statistical methods, (iii) shape fitting methods, and (iv) shape recognition methods.

6. A method according to claim 2 wherein the actual data set comprises a data cloud.

7. A method according to claim 6 wherein the database of different pre-determined data sets comprises data clouds generated by at least one from the group consisting of: (i) computer simulations that are performed in a virtual environment, and (ii) experimentally-derived laboratory data.

8. A method according to claim 7 wherein the step of comparing the actual data cloud with a database of different pre-determined data clouds is conducted using at least one from the group consisting of: (i) mathematical methods, (ii) statistical methods, (iii) shape fitting methods, and (iv) shape recognition methods.

9. A method according to claim 1 wherein comparing the actual data set with the plurality of different pre-determined data sets in the database includes comparing the actual data set with a second data set reflecting the desired orientation of the first joint prosthesis vis-à-vis the second, mating joint prosthesis.

10. A method according to claim 1 wherein the first joint prosthesis comprises an acetabular cup disposed in the pelvis.

11. A method according to claim 1 wherein the second, mating joint prosthesis comprises a femoral stem, and further wherein the femoral stem comprises an element mounted thereto.

12. A method according to claim 1 wherein the range of motion permitted between the second, mating joint prosthesis and the first joint prosthesis is tracked with a sensor positioned on at least one of the first joint prosthesis, the second, mating joint prosthesis, a bone carrying the first joint prosthesis and a bone carrying the second, mating joint prosthesis.

13. A method according to claim 1 wherein the device comprises an impactor positioned on the second joint prosthesis for engaging portions of the first joint prosthesis and moving the first joint prosthesis into a new orientation.

* * * * *